United States Patent [19]
Graves et al.

[11] Patent Number: 5,376,073
[45] Date of Patent: Dec. 27, 1994

[54] LOCKING SAFETY NEEDLE ASSEMBLY

[75] Inventors: Arlinda Graves, White Plains, N.Y.;
Niall Sweeney, Rutherford, N.J.

[73] Assignee: Becton, Dickinson and Company, Franklin Lakes, N.J.

[21] Appl. No.: 979,959

[22] Filed: Nov. 23, 1992

[51] Int. Cl.⁵ ............... A61M 37/00; A61M 5/00; A61M 25/00
[52] U.S. Cl. ........................ 604/86; 604/88; 604/263; 604/283
[58] Field of Search ............ 604/164, 167, 169, 283, 604/905, 86, 88, 192, 263

[56] References Cited

U.S. PATENT DOCUMENTS

| | | | |
|---|---|---|---|
| Re. 33,617 | 6/1991 | Ogle, II | 604/192 |
| 4,123,091 | 10/1978 | Cosentino et al. | 285/39 |
| 4,790,829 | 12/1988 | Bowden et al. | 604/244 |
| 4,792,163 | 12/1988 | Kulle | 285/88 |
| 4,826,486 | 5/1989 | Palsrok et al. | 604/174 |
| 4,838,871 | 6/1989 | Luther | 604/192 |
| 4,946,445 | 8/1990 | Lynn | 604/192 |
| 4,950,260 | 8/1990 | Bonaldo | 604/283 |
| 4,966,588 | 10/1990 | Rayman et al. | 604/165 |
| 4,981,469 | 1/1991 | Whitehouse et al. | 604/86 |
| 5,135,509 | 8/1992 | Olliffe | 604/192 |
| 5,137,524 | 8/1992 | Lynn et al. | 604/283 |
| 5,139,483 | 8/1992 | Ryan | 604/86 |
| 5,199,947 | 4/1993 | Lopez et al. | 604/56 |
| 5,207,667 | 5/1993 | Walker et al. | 604/283 |
| 5,248,306 | 9/1993 | Clark et al. | 604/283 |
| 5,282,794 | 2/1994 | Propp | 604/283 |
| 5,290,222 | 3/1994 | Feng et al. | 604/86 |

FOREIGN PATENT DOCUMENTS 9005559  5/1990  WIPO ................. 604/283

*Primary Examiner*—John D. Yasko
*Assistant Examiner*—Adam J. Cermak
*Attorney, Agent, or Firm*—Vincent A. Castiglione

[57] ABSTRACT

A safety needle assembly is provided for locking a hypodermic syringe to a fitting of an intravenous set. The assembly includes a shield with a needle cannula mounted therein. A latch is pivotably mounted to the needle shield for rotation about an axis extending generally orthogonal to the needle cannula. The latch includes a locking flange having a slot for engagement with the fitting of the intravenous set. The latch can be lockingly engaged into a position for securely retaining the safety needle assembly to the fitting, and includes a resiliently deflectable finger for urging the latch into a fully opened condition in response to disengagement of the lock.

10 Claims, 5 Drawing Sheets

LOCKING SAFETY NEEDLE ASSEMBLY

BACKGROUND OF THE INVENTION

1. Field of the Invention

The subject invention relates to a safety needle assembly that can be safely, easily and securely locked in communication with a fitting of an intravenous administration set.

2. Description of the Prior Art

Intravenous sets are widely used in the prior art to provide intravenous fluid communication with a patient. The prior art intravenous set includes a needle cannula for insertion into a vein of the patient. The needle cannula communicates with one end of a flexible plastic tube, while the opposed end of the tube is connectable to a flexible bag or bottle containing a fluid to be administered to the patient.

A prior art intravenous set may also include a fitting to which a hypodermic syringe may be "piggybacked" for administering parenteral drugs to a patient. For example, a Y-site is a Y-shaped plastic fitting having an inlet leg, an outlet leg and an injection leg. The injection leg of the Y-site is covered by a diaphragm which can be pierced by the needle cannula of a syringe carrying the parenteral drug. The injection leg and the outlet leg of the prior art Y-site typically are collinear with one another, while the inlet leg typically is aligned at approximately 30°–45° to the injection leg.

In use, a needle cannula of a hypodermic syringe carrying the parenteral drug to be administered is pierced through the membrane or septum on the injection leg of the Y-site. The hypodermic syringe is used in the standard manner to inject a selected dose of the parenteral drug into the injection leg. The drug is then transported to the patient by the fluid flowing from the inlet leg, through the outlet leg an toward the patient. A hypodermic needle connected to a lower volume intravenous set, sometimes called a piggyback set, is often used for introducing medication through the septum. Although this specification recites providing medication through the septum using a syringe it is understood that many fluid delivery devices can be used to provide secondary fluid to the needle which pierces or passes through the septum.

The potential for accidental needle sticks is further reduced by prior art needle cannulas having a rigid generally cylindrical shield mounted concentrically around the needle cannula. The shield defines a diameter large enough to telescope over an injection leg on an intravenous set as the needle cannula enters the fitting. Some such shields are provided with at least one axial extending opening for receiving the inlet leg of a Y-site as remaining portions of the shield are telescoped over the injection leg. A protective shield of this general type is shown, for example, in U.S. Pat. No. Re. 33,617.

Although prior art protective shields, as described above, can reduce the probability of accidental needle sticks, the open end of the axially extending openings still offer a potential for contact with the needle cannula. Additionally, a source of intravenous fluid intended for connection to a prior art intravenous fitting can be accidentally disengaged either before its initial use or between successive uses, thereby creating the potential for contamination of the needle cannula and/or loss of medication.

SUMMARY OF THE INVENTION

The subject invention is directed to a safety needle assembly for helping to prevent contamination of a needle cannula or accidental needle sticks and for lockingly retaining a needle cannula to a fitting of an intravenous set. The safety needle assembly includes a rigid needle shield disposed around a needle cannula to be injected into a fitting of an intravenous set.

The needle shield may include a proximal end for connection to a needle hub, such that the needle hub can be removably connected to a syringe barrel or other delivery device, such as a piggy-back intravenous set. Distal portions of the shield are dimensioned to protectively surround the needle cannula. The needle shield may further include at least one slot or opening extending from the distal end toward the proximal end and dimensioned to receive the inlet leg of a Y-site for an intravenous set. Thus, the needle shield may be telescoped over the injection leg of the Y-site with an alignment that permits the inlet leg of the Y-site to pass into the opening or slot at the distal end of the shield.

The locking safety needle of the subject invention further includes a latch for securely but releasably locking the needle cannula and needle shield to a fitting of an intravenous set. The latch may be moveable relative to the needle shield between a first position where the needle shield and needle cannula may be mounted to or removed from the fitting, and a second position where the needle shield and needle cannula are securely locked on the fitting.

The latch of the subject safety needle assembly may include a pivot arm hingedly mounted to the needle shield for rotation about an axis orthogonal to the needle cannula. The latch may further include a locking flange for selectively engaging a portion of the fitting. The locking flange may include a slot defining a width large enough to receive a portion of the fitting, but preferably small enough to prevent passage of the fitting therethrough. Thus, relative movement between the locking flange and the fitting can be prevented or minimized.

The safety needle assembly may further include locking means for securely, but releasably, retaining the latch in its locked condition. For example, the locking means may include a locking projection for secure locked retention with a portion of the needle shield. Preferably, the locking means is dimensioned to provide audible and tactile indication of both locking and unlocking.

The latch may further include biasing means for urging the latch away from the needle shield when the latch is in an unlocked condition relative to the needle shield. The biasing means may comprise a resilient cantilevered finger disposed on either the latch or the shield. Thus, the latch is clearly and distinctly moveable between either of two extreme positions for selectively locking the safety needle assembly to a fitting or permitting relative mounting or dismounting therefrom.

The tactile and audible locking indication combined with the biasing means provides redundant indication of the locking or unlocking of the safety needle assembly to a fitting. Thus, a health care worker can be positively assured that the needle shield and needle cannula are positively locked to a fitting, and accidental separation therefrom is positively prevented.

DETAILED DESCRIPTION OF THE PREFERRED EMBODIMENT

Figure 1:
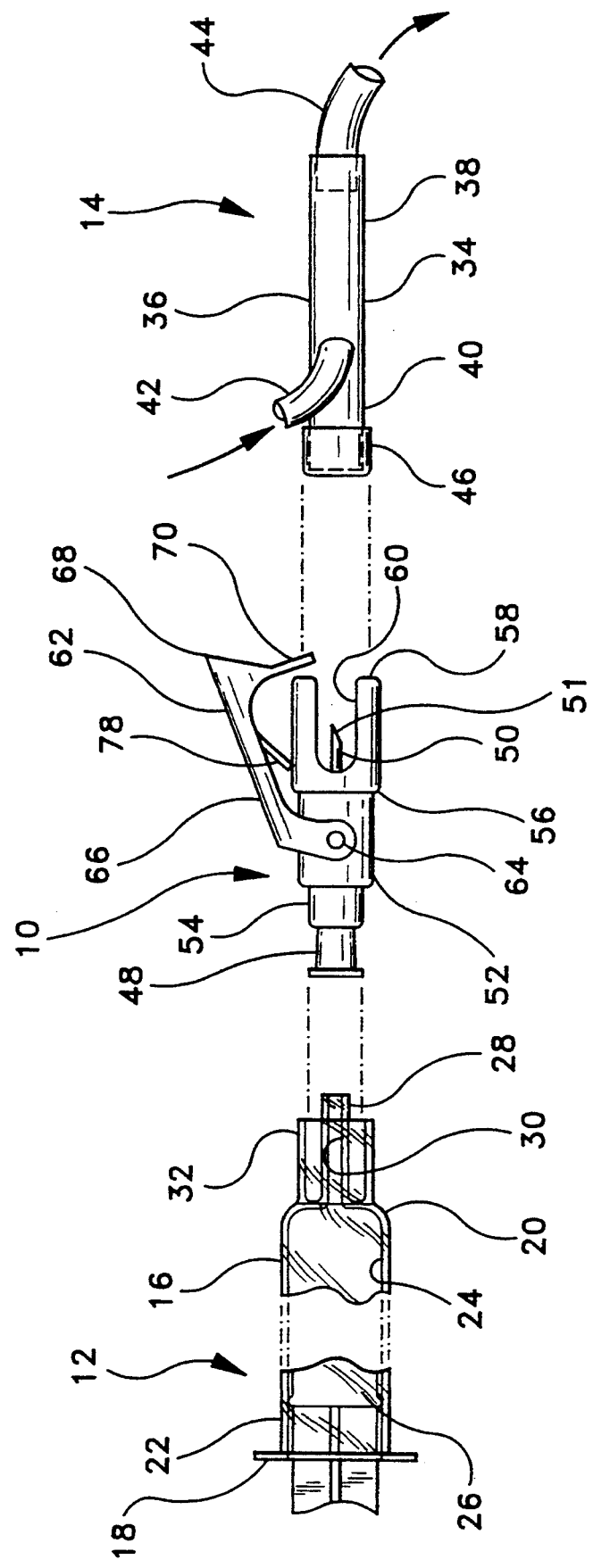
FIG. 1 is an exploded elevational view of a locking safety assembly in accordance with the subject invention in combination with a hypodermic syringe and a Y-site for an intravenous set.
Figure 2:
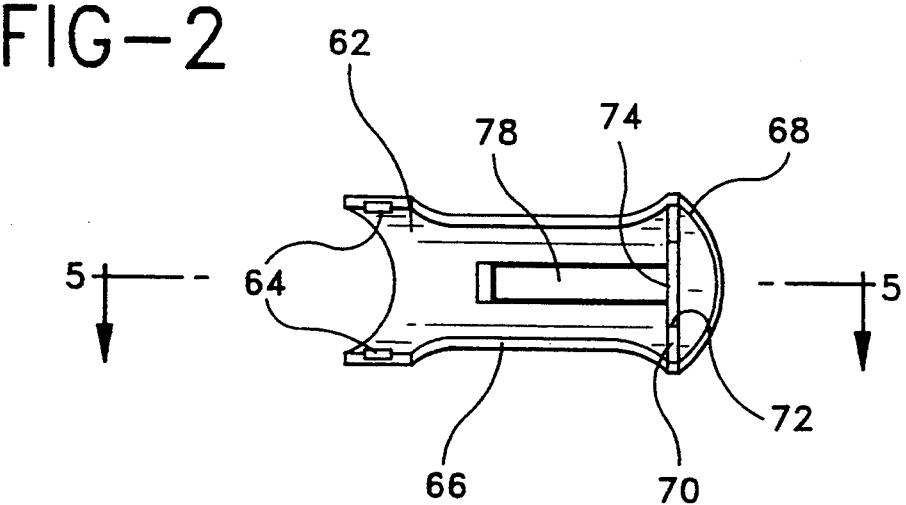
FIG. 2 is a bottom plan view of the latch of safety needle assembly.
Figure 3:
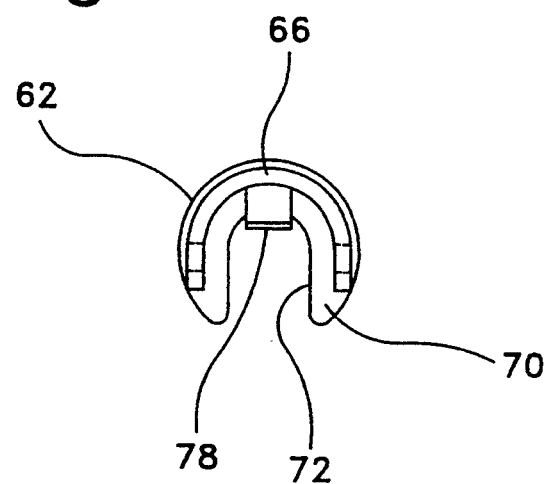
FIG. 3 is an end elevational view of the latch as viewed from the left side of FIG. 2.
Figure 4:
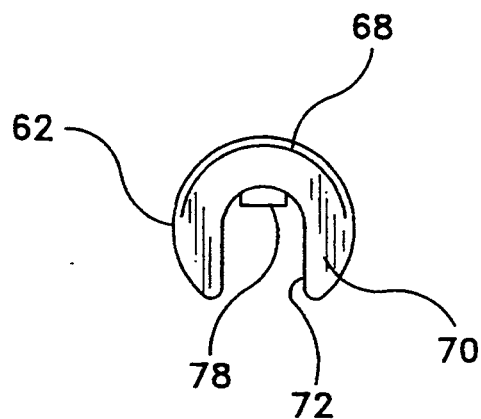
FIG. 4 is an end elevational view of the latch as viewed from the right side of FIG. 2.
Figure 5:
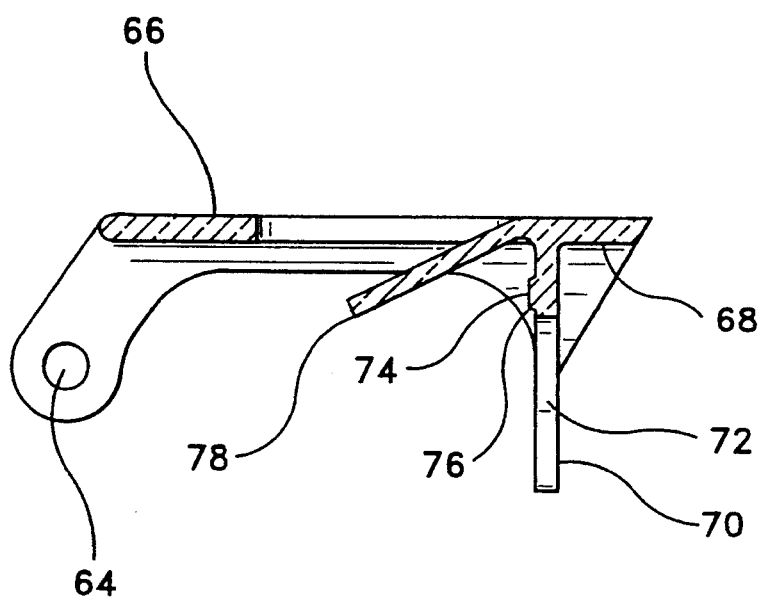
FIG. 5 is a cross-sectional view taken along line 5—5 in FIG. 2.

A lockable safety needle assembly in accordance with the subject invention is identified generally by the numeral 10 in FIGS. 1. Safety needle assembly 10 is intended for use with a hypodermic syringe 12 and an intravenous set 14.

Hypodermic syringe 12, or another fluid delivery device such as a piggyback intravenous set, can be used with lockable safety needle assembly 10. Syringe 12 includes a generally cylindrical syringe barrel 16 having an open proximal end 18, a distal end 20 and a cylindrical well 22 extending therebetween and defining a fluid receiving chamber 24 within the syringe barrel. A plunger 26 is slidably moveable in fluid-tight engagement within the cylindrical wall of syringe barrel 16 for urging fluid in the chamber toward distal end 20. The distal end of syringe barrel 16 includes a tip 28 having a passage 30 extending therethrough and communicating with chamber 24. A generally cylindrical collar 32 is unitarily formed on the distal end of syringe barrel 16 in spaced concentric relationship about the tip 28. The inner surface of collar 32 is provided with an array of internal threads for threadedly receiving the hub of a needle assembly, as explained herein.

Intravenous set 14 includes a Y-site 34 having an inlet leg 36, an outlet leg 38 and an injection leg 40. Inlet leg 36 is fixedly connected to an inlet tube 42 which extends to Y-site 34 from a supply of fluid to be delivered intravenously to a patient. Outlet leg 38 is fixedly connected to an outlet tube 44 for delivering the fluid to the patient. Injection leg 40 is a port for delivering a parenteral medication intravenously to the patient. More particularly injection leg 40 includes a barrier such as a pre-slit septum or pierceable septum such as barrier 46 for sealing the injection leg 40. The pierceable septum 46 is penetrable by a needle cannula to enable selective communication of a parenteral medication through the injection leg 40 and into the stream of fluid being delivered intravenously to the patient. In the case of a pre-slit septum the distal end of the needle cannula can be blunt or unsharpened because it will not be necessary for the needle to pierce the septum but just to pass through the slit. A pre-slit septum and blunt cannula are described in U.S. Pat. No. 4,790,829.

Lockable safety needle assembly 10 of the subject invention includes a needle hub 48 having a needle cannula 50 securely connected thereto. Needle cannula 50 includes distal end 51 which can be sharpened or blunt depending on the type of septum on the Y-site. The needle hub 48 is threadedly engageable with the collar 32 at the distal end of syringe barrel 16. Thus, threaded connection of hub 48 to collar 32 enables fluid communication from chamber 24 through passage 30 and through needle cannula 50.

The lockable safety needle assembly further includes a rigid needle shield 52 having a generally tubular base 54 securely and permanently mounted over a distal region of needle hub 48. A rigid generally cylindrical sheath 56 projects distally from the base of shield 52 a sufficient distance to protectively surround needle cannula 50. The sheath includes a distal end 58 and a pair of opposed openings 60 extending proximally to a location intermediate distal end 58 and base 54.

Figure 8:
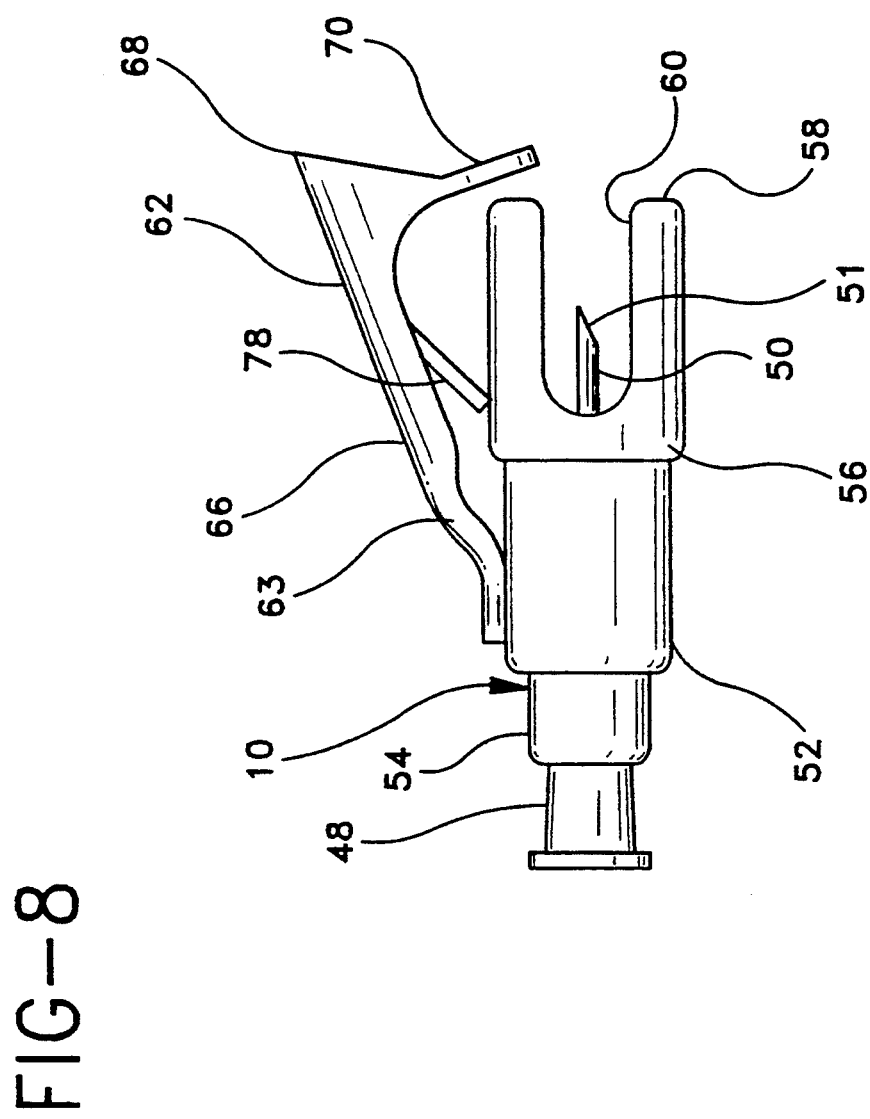
FIG. 8 is a side elevational view of the safety needle assembly of the subject invention wherein the pivot arm is connected to the shield through a living hinge.

Lockable safety needle assembly 10 Further includes a latch 62 hingedly connected to shield 52 at a pivot location 64 intermediate openings 60 and base 54. Latch 62 is hingedly mounted for rotation about an axis orthogonal to needle cannula 50 and lying in or parallel to a plane passing centrally through openings 60. It is also within the purview of this invention to include a plastic living hinge such as living hinge 63 in FIG. 8, to connect the latch and the shield for allowing pivoted rotation of the latch with respect to the shield.

Latch 62, as shown most clearly in FIGS. 2-5, includes a pivot arm 66 which extends generally distally from pivot point 64 and terminates in an actuating projection 68 which is dimensioned and configured to enable the pivoting movement to be generated easily by a thumb or a forefinger. A locking flange 70 extends generally orthogonally from pivot arm 66 in proximity to actuating projection 68. Locking flange 70 is characterized by a slot 72 dimensioned to receive outlet leg 38 of Y-site 34.

Figure 7:
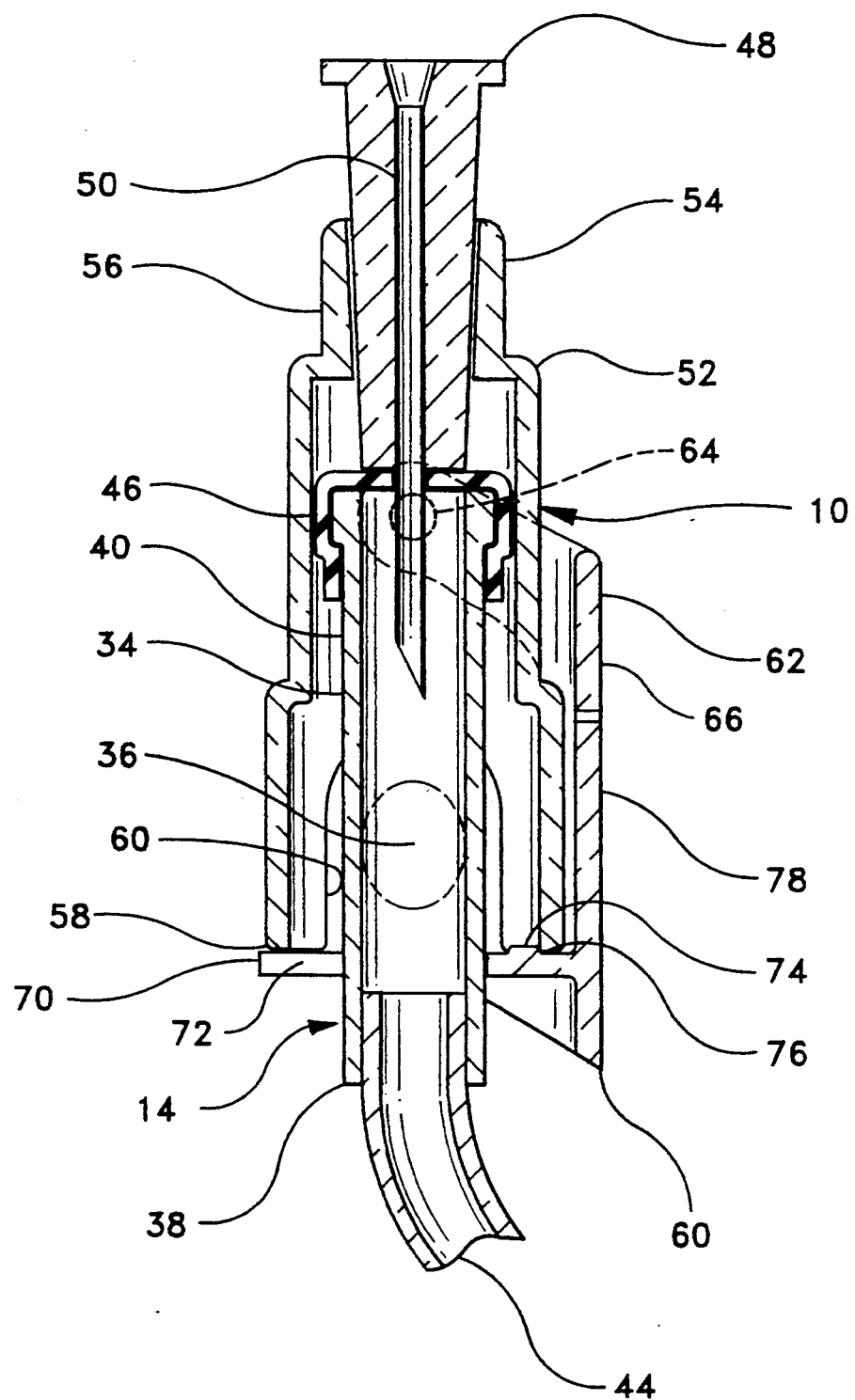
FIG. 7 is a cross-sectional view taken along line 7—7 in FIG. 6.

Locking flange 70 also includes a locking projection 74 generally facing pivot point 64 and spaced from pivot arm 66 by a distance to enable locked engagement of distal end 58 of sheath 56 therebetween as shown in FIG. 7. Locking projection 74 is of generally tapered frusto-conical configuration with a ramped side 76. In use, rotation of pivot arm 66 toward sheath 56, urges ramped side 76 of locking projection 74 into distal end 58 of sheath 56. Ramping forces cause sufficient deflection of locking flange 70 to enable further rotation of pivot arm 66 toward sheath 56. After sufficient rotation, locking projection 74 will clear distal end 58 of sheath 56, and locking flange 70 will resiliently return toward an undeflected condition against an inner surface of sheath 56. The ramped side of locking projection 74 also enables locking flange 70 to deflect in response to pivoting movement of latch 62 away from sheath 56. This deflection of locking flange 70 enables locking projection 74 to clear distal end 58 of sheath 56. The deflection and subsequent locked engagement of locking flange 70 with distal end 58 of sheath 56 can be configured to provide a distinct audible and/or tactile indication of the locked condition of latch 62 relative to sheath 56. Similarly, the deflection and subsequent resilient return of locking flange 70 in response to opening forces exerted on latch 62 also generates a distinct audible and tactile indication of the opened condition.

To facilitate complete opening of needle assembly 10, latch 62 is provided with a resiliently deflectable finger 78 projecting angularly from a region of pivot arm 66 in proximity to locking flange 70. In an unbiased condition, deflectable finger 78 is aligned to pivot arm 66 at an angle between approximately 20°-30°. However, finger 78 is resiliently deflected into substantially coplanar alignment with pivot arm 66 when latch 62 is urged into locked engagement with distal end 58 of sheath 56. Upon disengagement of locking projection 74 from distal end 58 of sheath 56, the resiliency of finger 78 urges latch 62 into its opened condition as shown in FIG. 1.

Lockable safety needle assembly 10 can be used by initially connecting the needle hub 48 to collar 32 at distal end 20 of hypodermic syringe 12. Lockable safety needle assembly 10 may then be employed with Y-site 34 of intravenous set 14 by aligning openings 60 in sheath 56 with inlet leg 36 of Y-site 34. Sheath 56 is then telescoped over Y-site 34 sufficiently for the sharp distal end of needle cannula 50 to pierce and pass through pierceable septum 46 on injection leg 40, and for inlet leg 36 of Y-site 34 to be engaged in opening 60 of sheath 56. As previously mentioned, if the Y-site includes a pre-slit septum the distal end of the needle may be blunt rather than sharp.

After full seating of sheath 56 on the injection leg of Y-site 34, latch 62 is rotated about pivot point 64 and toward sheath 56. Rotation of latch 62 causes finger 78 to deflect, and causes regions of locking flange 70 on opposite sides of slot 72 to engage outlet leg 38 of Y-site 34. This engagement will prevent movement of Y-site 34 and needle shield 52 relative to one another.

Figure 6:
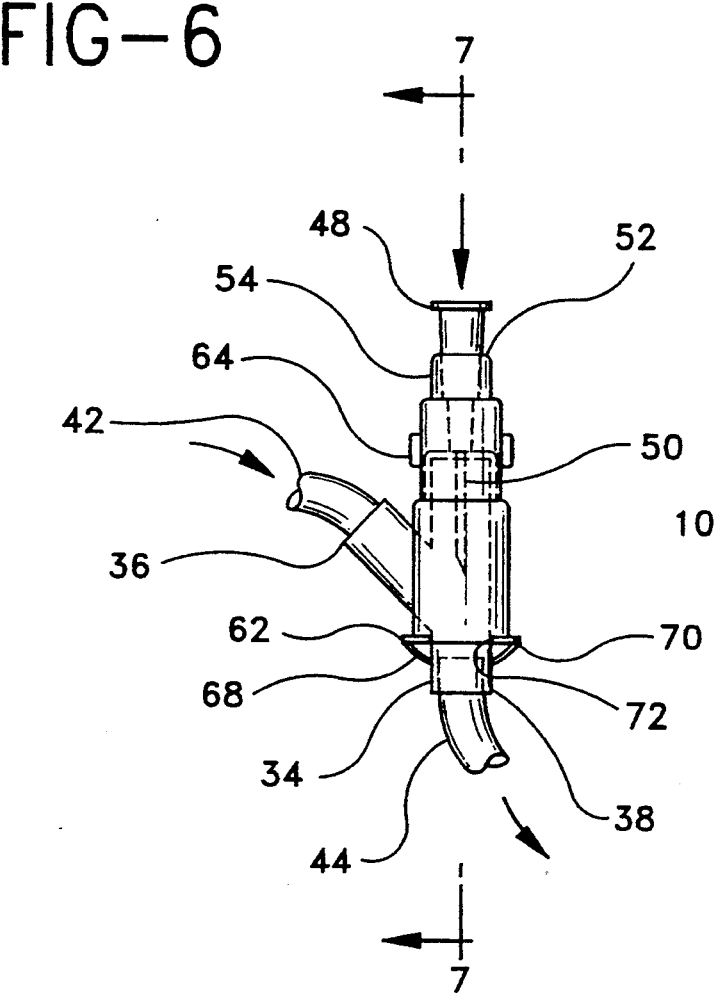
FIG. 6 is a side elevational view of the safety needle assembly of the subject invention locked to a Y-site.

The needle shield assembly 52 may be locked in the fully seated position as shown in FIGS. 6 and 7 by engagement of locking projection 74 with distal end 58 of sheath 56. In this regard, ramped forces generated by engagement of side 76 of locking projection 74 with distal end 58 of sheath 56 causes outward deflection of locking flange 70. However, after sufficient advancement of locking projection 72 relative to distal end 58 of sheath 56, locking flange 62 will preferably audibly and tactily snap into locked engagement with distal end 58 of sheath 56. This locked engagement of latch 62 will prevent unintended separation of latch 62 from Y-site 34. Disengagement of lockable safety needle assembly 10 from Y-site 34 is enabled only by exerting forces on actuating tab 68 to urge latch 62 away from sheath 56. These forces will cause locking flange 68 to deflect sufficiently for locking projection 74 to clear distal end 58, after which point finger 78 will resiliently return toward an undeflected condition, and thereby urge latch 62 into a fully opened condition as illustrated in FIG. 1.

What is claimed is:

1. A safety needle assembly for securely connecting a needle cannula to an intravenous fitting, comprising: a protective shield having a base for secure mounting around a needle cannula, a rigid sheath projecting from said base a sufficient distance for protectively surrounding said needle cannula, said sheath having a distal end dimensioned for receiving at least a portion of said intravenous fitting therein; and a latch having means for lockingly engaging said intravenous fitting, said latch mounted to said protective shield for pivoting movement between a first position where said latch lockingly engages said intravenous fitting received in said sheath and a second position where said latch is spaced from said intravenous fitting for enabling relative movement between said fitting and said sheath, said latch including a pivot arm having an end pivotably connected to said protective shield, and a locking flange projecting from a plan defined by said pivot arm at a location spaced from said pivotable connection so said protective shield, said means for lockingly engaging including said locking flange being dimensioned and configured to accepting said intravenous fitting within said sheath, wherein said means for lockingly engaging said intravenous fitting includes a locking projection on said locking flange for releasably engaging said distal end of said sheath.

2. A safety needle assembly for securely connecting a needle cannula to an intravenous fitting, comprising: a protective shield having a base for secure mounting around a needle cannula, a rigid sheath projecting from said base a sufficient distance for protectively surrounding said needle cannula, said sheath having a distal end dimensioned for receiving at least a portion of said intravenous fitting therein; and a latch having means for lockingly engaging said intravenous fitting, said latch mounted to said protective shield for pivoting movement between a first position where said latch lockingly engages said intravenous fitting received in said sheath and a second position where said latch is spaced from said intravenous fitting for enabling relative movement between said fitting and said sheath, said latch including a pivot arm having an end pivotably connected to said protective shield, and a locking flange projecting from a plane defined by said pivot arm at a location spaced from said pivotable connection to said protective shield, said means for lockingly engaging including said locking flange being dimensioned and configured to accepting said intravenous fitting within said sheath, further comprising biasing means for urging said latch into an opened position for facilitating engagement and disengagement of said safety needle assembly with said intravenous fitting.

3. A safety needle assembly for securely connecting a needle cannula to an intravenous fitting, comprising: a protective shield having a base for secure mounting around a needle cannula, a rigid sheath projecting from said base a sufficient distance for protectively surrounding said needle cannula, said sheath having a distal end dimensioned for receiving at least a portion of said intravenous fitting therein; and a latch having means for lockingly engaging said intravenous fitting, said latch mounted to said protective shield for pivoting movement between a first position where said latch lockingly engages said intravenous fitting received in said sheath and a second position where said latch is spaced from said intravenous fitting for enabling relative movement between said fitting and said sheath, said latch including a pivot arm having an end pivotably connected to said protective shield, and a locking flange projecting from a plane defined by said pivot arm at a location spaced from said pivotable connection to said protective shield, said means for lockingly engaging including said locking flange being dimensioned and configured to accepting said intravenous fitting within said sheath, further comprising an actuating tab defining an end portion of said pivot arm remote from said pivotable connection to said protective shield, said actuating tab being dimensioned to enable manual engagement for moving said latch, wherein said biasing means comprises a deflectable finger with at least a portion of said safety needle assembly for urging said latch into said second position.

4. A safety needle assembly for secure mounting to a Y-site of an intravenous set, said Y-site having a tubular inlet leg, a tubular outlet leg and a tubular injection leg angularly aligned to at least one of said inlet and outlet legs, said safety needle assembly comprising:

a cannula assembly including a needle hub for mounting to a fluid delivery device and a needle cannula projecting distally from said hub;

a protective shield having opposed proximal and distal ends, said proximal end defining a base securely mounted to said needle hub, a rigid sheath projecting from said base distally beyond said needle cannula, said sheath being spaced from said needle cannula sufficiently for receiving said injection leg of said Y-site, at least one opening extending from said distal end of said sheath toward said proximal end for receiving said inlet leg of said Y-site; and a latch having a pivot arm pivotably connected to said protective shield and a locking flange projecting from said pivot arm for lockingly engaging said Y-site, said locking flange including a locking projection engageable with said distal end of said protective shield for securely but releasably locking said Y-site in fixed position relative to said protective shield and said needle cannula.

5. The safety needle of claim 4 wherein said needle cannula includes a sharpened distal end.

6. The safety needle of claim 4 including a living hinge between said pivot arm and said protective shield wherein said pivot arm is pivotably connected to said protective shield through said living hinge.

7. The safety needle assembly of claim 4, wherein said locking flange includes a slot extending therein for receiving said outlet leg of said Y-site.

8. The safety needle assembly of claim 4, wherein said locking projection is ramped for generating deflection of said locking flange prior to locked engagement with said protective shield, said locking flange being audibly returnable toward an undeflected condition for locked engagement with said protective shield.

9. The safety needle assembly of claim 4 further comprising biasing means for urging said pivot arm away from said sheath.

10. The safety needle assembly of claim 9, wherein said biasing means comprises a resilient finger unitarily molded with said latch for urging said pivot arm away from said sheath.

* * * * *